(12) United States Patent
Ghosh et al.

(10) Patent No.: US 7,588,932 B2
(45) Date of Patent: Sep. 15, 2009

(54) INSERT DEVICE FOR CULTURING CELLS

(75) Inventors: Deepa Ghosh, Maharashtra (IN); Pushpa Chaudhary, Maharashtra (IN)

(73) Assignee: Reliance Life Sciences Pvt. Ltd., Maharashtra (IN)

( * ) Notice: Subject to any disclaimer, the term of this patent is extended or adjusted under 35 U.S.C. 154(b) by 767 days.

(21) Appl. No.: 11/144,491

(22) Filed: Jun. 3, 2005

(65) Prior Publication Data
US 2006/0223174 A1    Oct. 5, 2006

(30) Foreign Application Priority Data
Mar. 31, 2005    (IN) .................. 399/MUM/2005

(51) Int. Cl.
*C12M 3/06* (2006.01)
*C12M 1/22* (2006.01)
(52) U.S. Cl. .............. 435/297.5; 435/288.3; 435/305.1; 422/101
(58) Field of Classification Search .............. 435/297.1, 435/297.5, 288.3, 305.1; 422/101; 210/495; 38/102.2; 160/380
See application file for complete search history.

(56) References Cited

U.S. PATENT DOCUMENTS

| | | | | |
|---|---|---|---|---|
| 1,829,867 A | * | 11/1931 | Koster | 359/892 |
| 4,400,258 A | * | 8/1983 | Hans-Jurgen et al. | 204/415 |
| 4,608,342 A | * | 8/1986 | Nees | 435/401 |
| 5,409,832 A | * | 4/1995 | Pocock | 435/288.3 |

* cited by examiner

*Primary Examiner*—William H Beisner
(74) *Attorney, Agent, or Firm*—J. Harold Nissen; Lackenbach Siegel, LLP

(57) ABSTRACT

The present invention involves a device for culturing cells on removable membranes/sponges for the purpose of transplantation. The device includes a base plate with snaps and a ring, which fits into the base plate. The membrane/sponge of choice for culturing cells is placed on the base plate and fixed by the ring, which fits tightly to the base. The device is placed inside a suitable culture vessel or receptacle and the cell suspension is added within the insert device. The cells are retained on the membrane, which enables cell attachment and proliferation. Alternatively, small tissue explants can be placed on the membrane enabling cell migration and proliferation. Cells are cultured under standard conditions with regular media changes. Following shipping to the hospitals under appropriate conditions, the insert device would be dismantled and the membrane lifted and placed at the site of transplantation.

25 Claims, 1 Drawing Sheet

INSERT DEVICE FOR CULTURING CELLS

1. FIELD OF THE INVENTION

Figure 1:
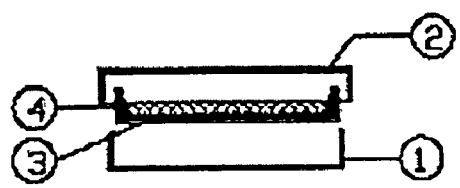

This invention relates to an insert device for growing cells on membranes. The present invention more particularly relates to a culture vessel assembly enabling the cells to proliferate and/or differentiate on membranes that may be used for transplantation.

2. BACKGROUND OF THE INVENTION

The potential for manipulating cells to repair or replace diseased or damaged tissue has generated a great deal of excitement amongst scientific, medical and biotechnology community.

Current cell based therapies have the potential to generate replacement cells for a broad array of tissues and organs such as skin, cornea, cartilage and other kinds of tissues that require the delivery of their cells to the site of transplantation. This is feasible by growing the cells either as monolayers on suitable membranes (U.S. Pat. No. 5,693,332 specifically incorporated herein by reference) and/or differentiating into multi layers (US patent No. 2003/0208266A1 specifically incorporated herein by reference) before transplantation, or culturing the cells on foams or sponges which can then be transplanted. Several membranes including but not limited to amniotic membrane, polyurethane films are used for culturing cells, which are then transplanted on the patient. To the best of knowledge of the inventors, none of the commercially available inserts have a provision to use membranes of choice. This restricts the use of such commercial inserts as a choice for membrane based delivery of cells.

Currently, under laboratory conditions, the membranes meant for cell support and transplantation are cultured in tissue culture dishes. The membranes are held flat and taut using metallic rings. Transportation of these cultures per se in such dishes is not feasible because of their design which provides for air exchange and hence does not ensure leak proof transportation. Media spillage not only wastes the precious media but also increases the chances of contamination. It is desirable before transplantation, for safety reasons, that the cultures be rinsed with a buffered solution to ensure the removal of traces of the transport media which might contain harmful substances like DMSO, which is used for cryopreservation; or proteins of animal origin present in the transport media. Rinsing of membranes by direct addition of the wash buffer to the cells present on the membrane would result in some of the cells getting detached from the membrane.

Traditional culture vessels generally have a circular shape and can be either single dish or multiple dishes. U.S. Pat. No. 4,349,632 discloses a tissue culture cluster dish having different numbers of wells.

U.S. Pat. Nos. 4,871,674A and 5,026,649 describe cell culture inserts for culturing membranes. The aforesaid devices have the following disadvantages. For example, these inserts have a fixed membrane upon which cell attachment, growth and differentiation occurs. Since the membranes are fixed, it is not possible to use any other membranes of choice for culturing cells. Besides, these membranes can be removed from the insert only after cutting with scalpel, which might result in damage to the cells. The available inserts, meant for culturing cells in multiwell dishes are of small sizes and not suitable for culturing cells in large areas. The membranes available in these inserts are not indicated for transplantation, thereby restricting their use to only culturing cells.

3. SUMMARY OF THE INVENTION

Looking to the need of the art, the scientists of the present invention have developed a device for culturing cells on removable membranes or sponges which can be used for transplantation of cells which aid in regenerating or reconstituting the functionally deficient area.

The present invention solves the above setbacks and for the first time, provides a specially designed insert device, which is compact, portable, commercially viable and easy-to-use device with a provision to load membrane's of choice into the insert for the purpose of culturing the cells and transporting it to the recipients location for transplantation of cells which aid in regenerating damaged tissues.

In one aspect of the invention, membranes of choice can be loaded on the insert device for culturing cells. In the present insert device, the device is so designed that the snaps of the device allows the ring to be detached, thereby allowing the loading of membranes onto the device. The detached ring can then be reattached to the device ensuring the taut fixation of the membrane in the device.

In another aspect of the invention, the device with the membranes carrying the cells can be transported to the recipient's location for transplantation.

In another aspect of the present invention, the membrane can be either preformed or cast insitu on the insert device.

In still another aspect of the present invention, the insert device is transported with the cells placed in a culture vessel or a receptacle that contains transport media and is transported to the recipient. The transport media can either be frozen, or in the liquid form. To ensure aseptic transportation the dish is covered with a silicon cap and a lid. The whole assembly is placed inside a sterile pouch and transported under suitable conditions. Before using the cells, the insert with membrane can be rinsed in a suitable buffer to remove traces of transport media by serially inserting the insert device in wash buffer. The device is then dismantled and the membrane with the cells is transplanted on the tissue of choice.

In yet another aspect of the invention, handling of the insert device can be performed aseptically using forceps.

In achieving the above objects, the specially designed cell culture insert device according to the present invention includes; a circular ring, a flat base with snaps attached diagonally to the base. The flat circular base with snaps attached diagonally to the base is for carrying either a porous or non-porous membrane. The size and shape of the membrane would be either of the exact size and shape of the base or slightly larger than the base plate. For assembling the present insert device, the ring is placed with its notches aligned to the snaps and pressed gently so that the ring is fixed firmly to the base. The assembled insert device is then placed in an appropriate culture vessel or a receptacle containing the culture media for growing cells. The insert device containing cells attached to the membrane are placed inside a receptacle, which preferably holds the insert device in a secure fashion, thereby minimizing the chance of the cells being damaged during transportation.

The present insert device can be formed in different sizes and geometric configurations so as to be used with different sizes and shapes of the tissue culture vessels or receptacle. The insert device may be constructed from a non-toxic; inert, biocompatible material selected from the group of polyethylene, polypropylene, polybutylene, polystyrene and polycarbonate and/or a combination thereof.

The principal objective of the present invention is to provide an insert device for culturing cells on removable membranes, which would then be detached from the device and preferably administered to the patient in a manner that permits the cells to be implanted to the intended site used to reconstitute or regenerate the functionally deficient area.

In preferred embodiment, the thickness of the membrane is in the range of about 0.01 mm to 1 cm.

In another preferred embodiment, the membrane, can either be non-coated or coated with factors like ECM proteins.

It is generally advantageous in clinical setting that these membranes are held taut so as to maintain a smooth surface enabling uniform cell attachment and growth to avoid crinkling of the membranes as such crinkling would result in cells attaching in the crevices leading to non-uniform cell attachment.

The device of the present invention is developed in a manner where the chances of the membrane crinkling is avoided. The rings of the insert device are designed in the manner to maintain the tautness of the membranes during culture.

These, and other objects and features of this invention will be better understood and appreciated from the following detailed and the accompanying drawings.

4. BRIEF DESCRIPTION OF THE DRAWINGS

FIG. 1: is a perspective diagram depicting an example of the culture device containing a membrane in a standard culture vessel or receptacle according to the present invention.

Figure 2:

FIG. 2: is a view of the base plate

Figure 3:

FIG. 3: is an illustrated view of the snap

Figure 4:

FIG. 4: is a view of the ring

Figure 5:
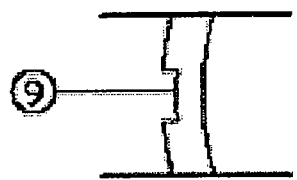

FIG. 5: is an illustrated view of the notch.

Figure 6:
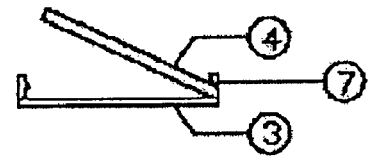

FIG. 6: is an illustrated view of the assembly of the device.

Figure 7:
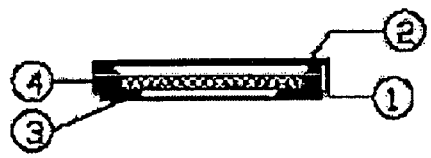

FIG. 7: is completely assembled view of the device.

5. DETAILED DESCRIPTION OF THE INVENTION

Several terms used in the invention are defined as follows.

DEFINITIONS

Throughout the specification of the application, various terms are used such as "top", "bottom", "upper", "lower", diagonal and the like. These terms are words of convenience in order to distinguish between different elements. While such terms are provided to explain the insert device relative to positions in which the insert device may normally be used, such terms are not intended to be limiting as to how the different elements may be utilized.

The term "cells" is used herein, for the purposes of the specification and claims, to mean one or more of live cells, cells comprising cellular aggregates, or an organized structure or network of cells forming a tissue, as apparent to those skilled in the art.

The term "medium or media" is used herein, for the purposes of the specification and claims, to mean a liquid solution which is used to provide sufficient nutrients (e.g., vitamins, amino acids, essential nutrients, salts, and the like) and properties (e.g., osmolarity, buffering) to maintain living cells (or living cells in a tissue) and support their growth.

Now referring to the drawings in general, it is apparent that the device for supporting the aforementioned cell culture insert, in accordance with the present invention, generally comprises a culture vessel or receptacle. The detailed relationship between the individual features of the culture vessel or receptacle is not critical to the invention. Additionally, the culture vessel or receptacle may be formed from a material, which provides the requisite rigidity and support for the inserts. As the specific character of the material does not in and of itself constitute the subject matter of the present invention, it should be apparent to those skilled in the art that a wide latitude of choice may be exercised in selecting a material suitable for formation and/or fabrication of the culture vessel.

The term membrane is used herein for the purpose of the specification and the claims, to mean sheet, film, foam, sponge or the like. The membrane used in the invention may either be of Biological Material, Semi synthetic Material or Synthetic Material. The term "Biological Material" include but not limited to Human amniotic membrane, acellularised dermis, small intestinal submucosonal (SIS) membrane and/or combination thereof. The term "Semi synthetic Material" include but not limited to Poly Lactic Acid (PLA), Poly Glycolic Acid (PGA), Hyaluronic Acid and/or a combination thereof.

The present disclosure relates to an insert device for culturing cells on membranes that may be used for transplantation.

The insert device of the present invention for growing tissue cultures shown in FIG. 1 includes, a tissue culture vessel containing a base (1) and a lid (2) and the insert device which comprises an upper ring (3) and the lower base (4). Although only a circular insert device is shown in a culture vessel or receptacle, it should be appreciated that the insert device could be square, hexagonal or any shape that fits the culture vessel or receptacle. The culture vessel does not form part of the present invention.

FIG. 2: illustrates the base plate of the insert each having an upper (5) and lower (6) portion. Two snaps (7) are located opposite to one another at approximately 180° apart on the flat circular base. The flat circular base supports the membrane as well as prevents the sagging of the membrane, which might occur due to the weight of the media present over the surface of the membrane. The base is typically transparent and may be molded from biocompatible or inert polymers, which have high clarity including and not limited to polycarbonate, polystyrene, or polypropylene. The membrane to be used in the device would be of the size and shape that fit the dimensions of the base plate. The shape of the base plate of the insert would vary with the shape of the culture vessel or receptacle to be used e.g. a circular base for a circular culture vessel or a square base for a square culture vessel.

The illustration in FIG. 3 embodies the snaps (7) attached to the base plate. The upper angled portion (8) ensures that the ring slides tightly into the base plate. Gentle outward extension of the snap leads to the release of the ring (3) from the base (4). The number of snaps in the base plate would vary with the shape of the base plate e.g. four snaps would be required for a square base plate.

Aseptic handling of the insert device of the present invention, as well as the membrane during assembly, culture and application on the patient is crucial for the success of cell and membrane based therapy and this has been achieved by the present invention. The ease of assembly and dismantling of the present device is ensured by the snaps, which were designed for handling with forceps.

Ring illustrated in FIG. 4 has a notch (9) on opposite sides. The height of the ring is such that the cells when added to the insert retains the media containing cells within the inner circumference of the insert device. This is to ensure that the added cells attach to the membrane and not to other areas outside the membrane. The shape of the ring would be similar to the base shape. Keeping in mind the shape of the base plate, the number of notches could vary to accommodate the number of snaps present on the base to ensure tight fixing of the ring to the base plate. During assembly, the notch is aligned with the snap and pushed gently for the ring to fix snugly to the base plate.

FIG. 5 shows the enlarged view of the notch. The tapering seen in the notch is required for the smooth sliding of the notch into the snap.

The assembly of the device is presented in FIG. 6. The orientation of the notch with the snap ensures the fixing of the ring to the notch.

FIG. 7 represents the assembled device. It is most desirable that no gap is available between the base plate and the top ring to ensure the tight fixing of the membrane.

The present inventors, keeping the following requirements in mind have designed the height of the snaps.

a) To ensure the availability of headspace in the assembled insert device permitting aseptic handling of the device with forceps.
b) The insert device on being transferred into the culture vessel or receptacle does not obstruct the closure of culture vessel or receptacle.

The insert device of the present invention comprises of moldable parts, which may be mass-produced from a variety of biocompatible or inert materials, including and not limited to polyethylene, polystyrene, polyethylene terepthalate, polycarbonate or polypropylene. The materials selected provide a small degree of resiliency for the purpose of providing ease of insertion of the ring into the base, as well as for the dismantling of the device.

In view of the foregoing descriptions and figures, it will become apparent to those of ordinary skill in the art that equivalent modifications thereof may be made without departing from the spirit and scope of this invention. Various features are set forth in the following claims.

We claim:

1. An insert device for use in transporting cells for transplanting of cells for regeneration or reconstituting a functionally deficient cell consisting of:
   i. a flat base and snaps attached to the base for carrying a removable membrane of choice or sponger for culturing of cells on said membrane;
   ii. a single ring provided with notches and with said aligned snaps for engaging said notches when pressed gently so that the snaps firmly fix said ring as said ring is being positioned to the base;
   iii. said notch being positioned on opposite sides of the ring and facing each other;
   iv. said snaps being located opposite to one another at approximately 180° apart from each other on the flat base; and
   v. a receptacle or culture vessel for containing a transportation medium.

2. An insert device according to claim 1 wherein said culture vessel includes media into which said insert device is placed for culturing cells.

3. An insert device according to claim 1 wherein said receptacle is provided for receiving the insert device containing the membrane with the cells for retaining the cells in a secured fashion, thereby minimizing the chance of the cells being damaged during transportation.

4. An insert device according to claim 3 wherein the transportation medium receives the insert-device for transportation to a recipient of the cell in the receptacle containing said transportation medium.

5. An insert device according to claim 1, wherein the snaps in combination with said notches alone, solely allows the ring to be detached, thereby allowing the loading of membranes onto the device, and the detached ring can then be reattached to the device ensuring the taut fixation of the membrane in the device.

6. The insert device according to claim 1 including means for culturing the cells during transporting of the cells, further comprises culturing cells on membranes which contain culturing media, which would then be cultured during transporting and detached from the device and administered to the patient in a manner that permits the cells to be implanted to the intended site used to reconstitute or regenerate a functionally deficient area.

7. The insert device according to claim 1, wherein the device provides specifically for aseptic handling and for this purpose the height of snaps is designed to ensure the availability of a headspace in the assembled insert device permitting said aseptic handling of the device with forceps.

8. The insert device according to claim 1, is further characterized by tapering the notch for the smooth sliding of the notch into the snap.

9. The insert device according to claim 1, wherein the cells are selected from one or more of live cells, cells comprising cellular aggregates, or an organized structure or network of cells forming a tissue.

10. An insert device for culturing cells on a removable membrane of choice or sponges for use in transporting cells for transplanting of cells for regeneration or reconstituting a functionally deficient cell consisting of:
    i. a membrane of choice, a flat base and snaps attached to the base for carrying said membrane;
    ii. a single ring provided with notches and with said aligned snaps for engaging said notches when pressed gently so that the snaps firmly fix said ring as said ring is being positioned to the base;
    iii. said notch being positioned on opposite sides of the ring and facing each other; and
    iv. said snaps being located in opposed positions to one another at approximately 180° apart from each other on the flat base.

11. The insert device according to claim 10, for culturing cells on membrane of choice, for therapeutic purpose wherein crinkling is avoided because pressure is created with the cooperation of the notches and snaps which provide for stretching in a single direction.

12. The insert device according to claim 10, wherein the membrane can be preformed or cast insitu on the insert device.

13. The insert device according to claim 10, wherein membrane is selected from the group consisting of sheet, film, foam, sponge or a combination thereof.

14. The insert device according to claim 13, wherein the membrane is selected from the group consisting of Biological Material, Semi-synthetic Material or Synthetic Material.

15. The insert device according to claim 14, wherein the Biological Material is selected from the group consisting of Human amniotic membrane, a cellularised dermis, small intestinal submucosonal (SIS) membrane and/or combinations thereof.

16. The insert device according to claim 14, wherein the Semi synthetic Material is selected from the group consisting of Poly Lactic Acid (PLA), Poly Glycolic Acid (PGA), Hyaluronic Acid and/or a combination thereof.

17. The insert device according to claim 14, wherein the Synthetic Material is selected from the group consisting of polyethylene, polypropylene, polybutylene, polystyrene, polycarbonate, polyethylene-terepthalate and/or a combination thereof.

18. The insert device according to claim 10, wherein the thickness of the membrane is between about 0.01 mm to 1 cm.

19. The insert device according to claim 10, wherein the membrane is transparent, translucent or opaque.

20. The insert device according to claim 10, wherein the membrane is optionally coated with conventional coating material.

21. The insert device according to claim 10, wherein the device is made of non-toxic, inert, biocompatible material selected from the group of polyethylene, polypropylene, polybutylene, polystyrene, polycarbonate, polyethylene-terepthalate and/or a combination thereof.

22. The insert device according to claim 10, wherein the device is of different shapes such as circular, square, hexagonal or any other shape that fits in the culture vessel or receptacle.

23. The insert device of claim 10, wherein the ring has a thickness of about 1 mm and above.

24. The insert device of claim 10, wherein the flat base has a thickness of about 1 mm and above.

25. The insert device according to claim 10, wherein the number of notches vary to accommodate the number of snaps present on the base, to ensure tight fixing of the ring to the flat base, and wherein the number of notches and the number of snaps are always even.

* * * * *